United States Patent

Kappes et al.

[11] Patent Number: 5,385,736
[45] Date of Patent: Jan. 31, 1995

[54] TRANSDERMAL MELATONIN DELIVERY SYSTEM

[75] Inventors: Joan K. Kappes, Minneapolis; John R. Hart, Hugo, both of Minn.

[73] Assignee: Minnesota Mining and Manufacturing Company, St. Paul, Minn.

[21] Appl. No.: 90,330

[22] Filed: Jul. 12, 1993

[51] Int. Cl.$^6$ .............................................. A61F 13/02
[52] U.S. Cl. ................................... 424/448; 424/449; 514/546; 514/547
[58] Field of Search ................. 424/448, 449; 514/546, 514/547

[56] References Cited

U.S. PATENT DOCUMENTS

| Re. 24,906 | 12/1960 | Ulrich | 206/59 |
|---|---|---|---|
| 4,411,893 | 10/1983 | Johnson et al. | 424/181 |
| 4,600,723 | 7/1986 | Short et al. | 514/416 |
| 4,654,361 | 3/1987 | Samples et al. | 514/419 |
| 4,751,087 | 6/1988 | Wick | 424/449 |
| 4,945,103 | 7/1990 | Cohen | 514/419 |
| 5,059,426 | 10/1991 | Chiang | 424/449 |

FOREIGN PATENT DOCUMENTS

| 0438856A2 | 7/1991 | European Pat. Off. |
| 0518468A1 | 12/1992 | European Pat. Off. |
| 93/07870 | 4/1993 | WIPO |

OTHER PUBLICATIONS

*Headache* 1989, 29, 242 (Claustrat et al.).

*Primary Examiner*—D. Gabrielle Phelan
*Attorney, Agent, or Firm*—Gary L. Griswold; Walter N. Kirn; Douglas E. Reedich

[57] ABSTRACT

A pressure sensitive adhesive coated sheet material for delivering melatonin through the skin. The sheet material has a flexible backing bearing a pressure sensitive adhesive coating involving an acrylic copolymer, melatonin, 2-(2-ethoxyethoxy)ethanol, and optionally N,N-dimethyldodecylamine-N-oxide.

19 Claims, 1 Drawing Sheet

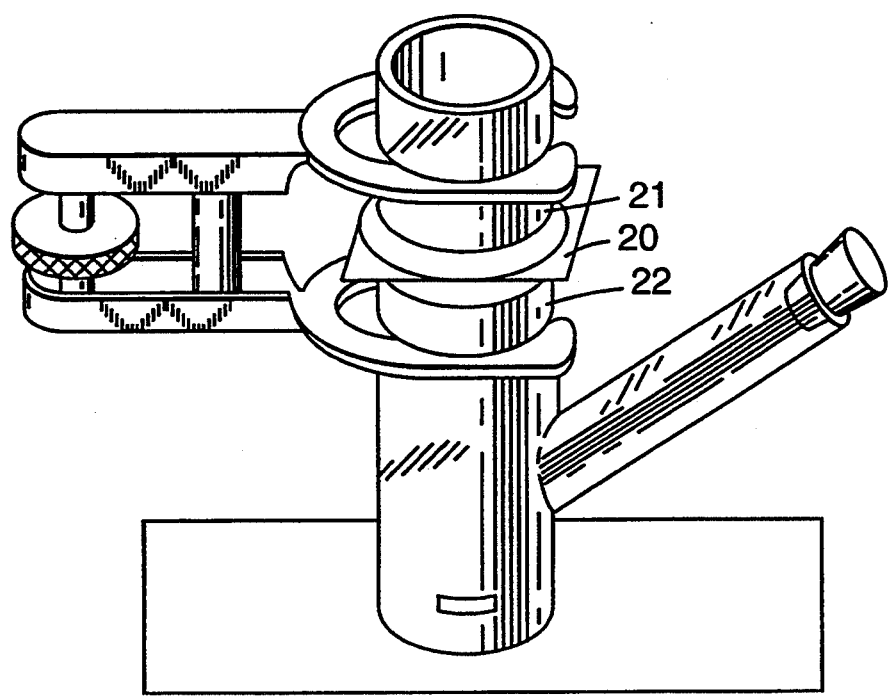

TRANSDERMAL MELATONIN DELIVERY SYSTEM

BACKGROUND OF THE INVENTION

1. Field of the Invention

This invention relates to transdermal drug delivery systems. In another aspect this invention relates to transdermal drug delivery systems containing melatonin.

2. Description of the Related Art

Transdermal drug delivery systems are designed to deliver a therapeutically effective amount of drug across the skin of a patient. Devices known to the art include reservoir type devices involving membranes that control the rate of drug release to the skin and devices involving a dispersion of the drug in a matrix such as a pressure sensitive adhesive. As the skin presents a barrier to the drug it is often desirable or necessary to incorporate certain materials that enhance the rate at which the drug passes through the skin. For any particular drug, however, the type of devices, the transdermal flux rate that is suitable, and the suitable formulation components are dependent upon the particular drug to be delivered.

Melatonin, N-[2-(5-methoxy-1H-indol-3-yl)ethyl]acetamide, is a hormone synthesized and secreted by the pineal gland. Melatonin shows a circadian variation with high nocturnal but low or undetectable diurnal plasma concentrations. Melatonin has been studied for a variety of therapeutic applications.

U.S. Pat. No. 4,600,723 (Short et al.) discloses the use of melatonin to alleviate or prevent the negative effects associated with disturbances in circadian rhythms of bodily performance and function which may occur for example in transfer of work patterns from day to night shift or rapid crossing of several times zones (jet lag).

U.S. Pat. No. 4,654,361 (Samples et al.) discloses the use of melatonin to lower intraocular pressure in a human having abnormally high intraocular pressure.

U.S. Pat. No. 4,945,103 (Cohen) discloses the use of melatonin to treat premenstrual syndrome.

European Patent Application 0 438 856 A2 (Fukuda et al.) discloses the use of melatonin to protect the skin against the influence of ultraviolet radiation.

European Patent Application 0 518 468 A1 (Zisapel) discloses the use of melatonin to prevent sudden infant death syndrome.

Decreased plasma melatonin levels in migraine patients have been reported in *Headache* 1989, 29, 241 (Claustrat et al.).

U.S. Pat. No. 4,411,893 (Johnson et al.) discloses the use of certain amine oxides to enhance the penetration of therapeutic agents into and through skin.

SUMMARY OF THE INVENTION

The present invention provides an adhesive coated sheet material comprising a backing bearing on one surface thereof a pressure sensitive adhesive coating comprising a homogeneous mixture of (i) a copolymer comprising
   (1) about 60 to 80 percent by weight of a monomeric acrylic or methacrylic acid ester of an alkyl alcohol containing 4 to 10 carbon atoms, based on the weight of all monomers in the copolymer;
   (2) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide, and N-vinyl-2-pyrrolidone, based on the weight of all monomers in the copolymer; and
   (3) about 15 to 35 percent by weight of vinyl acetate, based on the weight of all monomers in the copolymer;
(ii) a therapeutically effective amount of melatonin; and
(iii) a skin-penetration enhancing amount of 2-(2-ethoxyethoxy)ethanol.

The present invention also provides an adhesive coated sheet material as described above, further comprising a skin-penetration enhancing amount of N,N-dimethyldodecylamine-N-oxide.

This invention also provides a method of treating in an animal a condition capable of treatment by melatonin, comprising the steps of:

(i) providing an adhesive coated sheet material as described above;
(ii) applying the adhesive coated sheet material to the skin of the animal; and
(iii) allowing the adhesive coated sheet material to remain on the skin for a time sufficient to establish or maintain a therapeutically effective blood level of melatonin.

This invention also provides a method of preventing and/or relieving migraine headache.

BRIEF DESCRIPTION OF THE DRAWING

The drawing shows a perspective view of a diffusion cell used to determine transdermal flux of an adhesive coated sheet material of the invention.

DETAILED DESCRIPTION OF THE INVENTION

The present invention provides pressure sensitive adhesive coated sheet materials comprising a backing coated with a layer of pressure sensitive adhesive containing melatonin. Melatonin is present in an adhesive coated sheet material of the invention in a therapeutically effective amount. The amount that constitutes a therapeutically effective amount varies according to the condition being treated, the surface area of the skin over which the adhesive coated sheet material is to be placed, and on other components of the adhesive coating. Accordingly it is not practical to enumerate particular preferred amounts but such can be readily determined by those skilled in the art with due consideration of these factors. Generally, however, and also in embodiments intended for the treatment of migraine, melatonin is present in an amount of about 1 to 10 percent, preferably about 2 to 5 percent, by weight based on the total weight of the adhesive coating.

Suitable adhesives include acrylic copolymer pressure sensitive adhesives that comprise about 60 to 80 percent by weight, preferably 70 to 80 percent by weight (based on the total weight of all monomers in the copolymer) of a monomeric acrylic or methacrylic acid ester of an alkyl alcohol, the alkyl alcohol containing 4 to 10 carbon atoms, preferably 6 to 10 carbon atoms, more preferably about 6 to 8 carbon atoms, and most preferably 8 carbon atoms. Examples of suitable monomers are n-butyl, n-pentyl, n-hexyl, isoheptyl, n-nonyl, n-decyl, isohexyl, 2-ethyloctyl, isooctyl and 2-ethylhexyl acrylates. The most preferred monomeric acrylic acid ester is isooctyl acrylate. These adhesives further comprise from about 4 to 9 percent by weight (based on the total weight of all monomers in the copolymer) of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide, and N-vinyl-2-pyrrolidone. The preferred monomer is acrylamide. These adhesives further comprise from about 15 to 35 percent by weight, and preferably 15 to 25 percent by weight (based on the total weight of all the monomers in the copolymer) of vinyl acetate.

The above described adhesive copolymers can be prepared by methods well known to those skilled in the art and described for example, in U.S. Patent RE 24,906 (Ulrich), the disclosure of which is incorporated herein by reference. The polymerization reaction can be carried out using a free radical initiator such as an organic peroxide (e.g., benzoylperoxide) or an organic azo compound (e.g., 2,2'-azobis(2,4-dimethylpentanenitrile), available under the trade designation "Vazo 52" from DuPont).

Since pressure sensitive adhesives such as those described above are inherently rubbery and tacky and are suitably heat and light stable, there is no need to add tackifiers or stabilizers. However, such can be added if desired.

It has been found that the addition of certain excipients significantly enhances the rate of melatonin skin penetration in vitro measured using the hairless mouse skin model as described below. Hence, the adhesive coating further comprises 2-(2-ethoxyethoxy)ethanol. The 2-(2-ethoxyethoxy)ethanol is generally present in a skin-penetration enhancing amount, i.e., an amount effective to increase the rate of transdermal flux of melatonin in the Hairless Mouse Skin model described in detail below compared to an adhesive coated sheet material comprising a like adhesive coating absent the 2-(2-ethoxyethoxy)ethanol. Preferably the adhesive coating comprises about 30 to about 40 percent of 2-(2-ethoxyethoxy)ethanol by weight based on the total weight of the adhesive coating.

The adhesive coating optionally further comprises a skin-penetration enhancing amount of N,N-dimethyldodecylamine-N-oxide. Preferably the adhesive coating contains this compound in an amount of about 1 to 3 percent by weight based on the total weight of the adhesive coating.

A sheet material of the invention also comprises a backing. Suitable backing materials include conventional flexible backing materials used for pressure sensitive adhesive tapes, such as polyethylene, particularly low density polyethylene, linear low density polyethylene, high density polyethylene, randomly oriented nylon fibers, polypropylene, ethylene-vinyl acetate copolymer, polyurethane, rayon, and the like. Backings that are layered, such as polyethylene-aluminum-polyethylene composites are also suitable. The backing should be substantially inert to the ingredients of the adhesive coating.

Adhesive coated sheet materials of the invention can be prepared by combining dry adhesive, melatonin, and the excipients with a suitable organic solvent (e.g., heptane, isopropanol, methanol, or ethyl acetate depending upon the particular adhesive used) to afford a coating solution. The total solids content of the coating solution is preferably in a range of about 15 percent to about 40 percent by weight, and more preferably in the range of about 20 to about 35 percent by weight, based on the total weight of the coating solution. The mixture of dry adhesive, melatonin, excipient, and solvent is shaken at high speed until a homogeneous solution is obtained, and then allowed to stand to dissipate air bubbles. The resulting coating solution is knife coated onto a suitable release liner to provide a predetermined uniform thickness (e.g., a thickness sufficient to afford a dried pressure sensitive adhesive coating having a thickness of about 450 $\mu$m to about 650 $\mu$m) of the coating solution. Suitable release liners include conventional release liners comprising a known sheet material such as a polyester web, a polyethylene web, or a polystyrene web, or a polyethylene-coated paper, coated with a suitable silicone-type coating such as that available under the trade designation Daubert 164Z, from Daubert Co. The coated release liner is then dried and then laminated onto a backing material using conventional methods.

The adhesive coated sheet material of the invention can be made in the form of an article such as a tape, a patch, a sheet, a dressing or any other form known to those skilled in the art. Generally a sheet material is made in the form of a dosage unit such as a patch of a size suitable to deliver an appropriate preselected amount of melatonin through the skin. Generally a dosage unit has a surface area of about 1 cm$^2$ to about 40 cm$^2$.

The adhesive coated sheet material of the invention can be used to treat conditions capable of treatment with melatonin, e.g., migraine. Generally, a sheet material of the invention is applied to the skin of an animal (preferably a human) and allowed to remain for a time sufficient to establish or maintain a therapeutically effective blood level of melatonin in order to achieve the intended therapeutic effect.

The examples set forth below are intended to illustrate the invention.

Preparation of Isooctyl Acrylate: Acrylamide: Vinyl Acetate (74:6:20) Copolymer

Isooctyl acrylate (148 g), acrylamide (12 g), vinyl acetate (40 g), 2,2'azobis(2,4-dimethylpentanenitrile) (0.30 g, available from DuPont under the trade designation Vazo 52), ethyl acetate (310 g) and methanol (30.7 g) were added to a glass bottle. The bottle was purged with nitrogen for 3 minutes at a flow rate of 1 liter per minute. The bottle was sealed and placed in a rotating water bath at 45° C. for 29.5 hours to effect essentially complete polymerization. The resulting copolymer had a Brookfield viscosity of 27,500 centipoise.

A 25–30 percent solids solution of the copolymer in ethyl acetate:methanol (90:10) was coated onto a two-sided release liner using a knife coater and coating at 500 $\mu$m (20 mils). The adhesive coated liner was oven dried for 2 minutes at 43° C., for 2 minutes at 85° C. and for 2 minutes at 108° C. The dried adhesive was then stripped off the release liner and stored in a glass bottle.

Example 1

Melatonin (1.5 g; Biosynth AG, 9422 Staad, Switzerland) was combined with 2-(2-ethoxyethoxy)ethanol (17.5 g; available under the trade designation Transcutol from Gattefosse, 69800 Sazint Priest, France) in a glass beaker and stirred with a magnetic stirrer for 15 minutes to provide a homogeneous solution. Dry adhesive (30 g of isooctyl acrylate: acrylamide: vinyl acetate 74:6:20) was placed in a glass jar. The melatonin/2-(2-ethoxyethoxy)ethanol solution was added to the adhesive. N,N-dimethyl-dodecylamine-N-oxide (1.5 g; Stepan Europe, 38340 Voreppe, France) was added to the jar followed by 70:30 heptane:isopropanol (70 g). The glass jar was closed with a metal screw top then placed on a shaker set at 90 rpm for about 22 hours. After shaking the resulting formulation was allowed to stand for 1 hour to allow any air bubbles to dissipate. The formulation was knife coated at a thickness of 533 μm (21 mil) onto a silicone release liner. The resulting coated release liner was oven dried for 4 minutes at 43° C. for 2 minutes at 85° C. and for 2 minutes at 107° C. The resulting adhesive coating contained 60 percent by weight of the 74:6:20 isooctyl acrylate:acrylamide:vinyl acetate adhesive copolymer, 35 percent by weight of 2-(2-ethoxyethoxy)ethanol, 3 percent by weight of melatonin and 2 percent by weight of N,N-dimethyl-dodecylamine-N-oxide. The dried adhesive coated liner was allowed to stand at room temperature for 2 minutes then it was laminated onto the corona treated surface of a low density polyethylene film backing. The laminate was die cut into 3.0 cm$^2$ patches. Release rate of melatonin and penetration of melatonin through a hydrogel from these patches was tested according to the methods described below.

In-vitro Release Rate

The release liner was removed from 6 patches prepared in Example 1. One patch was placed adhesive side down in each of the 6 Sotax ® cells of a DISSOTEST CE6 dissolution apparatus (both available from Sotax SA, Bale, Switzerland) equipped with Diassamo 210 software (available from Safas, Monaco). Each cell was charged with 100 mL of a standard buffer solution (7.45 g potassium chloride, 1.7 mL concentrated hydrochloric acid, adjusted to a final volume of 1000 mL with demineralized water to give pH=1.72±0.03) which had been warmed to 37±1° C. The instrument parameters were set as follows: dissolution batch temperature at 37° C.; flow rate at 30 mL/min; analysis time at 30 hours; sampling every 60 minutes and wavelength 278 nm. The results are reported as the cumulative percent melatonin released and are summarized in the table below.

| | In-vitro Melatonin Release |
|---|---|
| Time (hours) | Cumulative % Melatonin Released |
| 1 | 26.2 ± 1.5 |
| 5 | 56.5 ± 1.2 |
| 10 | 77.8 ± 1 |
| 15 | 89.1 ± 0.6 |
| 20 | 95.7 ± 0.6 |
| 25 | 97.8 ± 0.2 |
| 30 | 100 |

In-vitro Penetration Through a Hydrogel

Hydrogel Preparation

A polyvinylpyrrolidone/cellulose acetate hydrogel for use in this assay can be prepared in the following manner. A 9.6 g portion of polyvinylpyrrolidone (average molecular weight of 360,000; available from Aldrich Chemical Company, Milwaukee, WI) is dried at 100° C. under vacuum for a minimum of 2 hours. The dried polyvinylpyrrolidone is blended in a jar with 2.4 g of cellulose acetate. A 120 mL portion of 9:1 (wt/wt) acetone/methanol is added and the jar is placed on a roller mixer overnight. A TEFLON ® brand polytetrafluoroethylene coated stainless steel spin-caster cylinder is lined with polyester, placed in the spin-caster and then purged with nitrogen for 20 minutes. The nitrogen line is removed, a 20 mL portion of the polyvinylpyrrolidone/cellulose acetate solution is injected into the cylinder, the nitrogen line is reattached and the spin-caster is run for 15 hours. The resulting dry hydrogel is removed from the cylinder and stored in a jar. Prior to use in this test method, the hydrogel is hydrated in deionized, deaerated water for at least 24 hours.

Buffer Preparation

A standard buffer solution was prepared by dissolving 1.625 g of sodium phosphate, dibasic heptahydrate, in 900 mL of water. Sodium phosphate, monobasic dihydrate, (0.634 g) and sodium chloride (7.72 g) were added and the final volume was brought to 1000 mL with water. If necessary, the pH was adjusted to 7.0±0.1 with either 6N sodium hydroxide or concentrated hydrochloric acid.

Procedure

A section of hydrated hydrogel was mounted in a diffusion cell of the type shown in the Drawing. The cell is modeled after those described in the literature, e.g., J. L. Cohen, R. B. Stoughton, *J. Invest. Derm.*, 62, 507 (1974) and R. B. Stoughton, *Arch. Derm.*, 99, 753 (1964). As shown in the Drawing, the hydrogel 20 was mounted between upper portion 21 and lower portion 22 of the cell.

Patches (3.0±0.1 cm$^2$) were die cut from the sheet material prepared in Example 1. The release liner was removed and the patches, one per cell in each of three cells, were adhered to the hydrogel.

The portion of the cell below the mounted hydrogel was completely filled with buffer solution such that the buffer solution contacted the hydrogel. The cells were placed in a constant temperature (37±1° C.) chamber and the magnetic stirrer was activated.

At each sampling point, the entire volume of buffer solution was removed then immediately replaced with a fresh portion of buffer solution. The solutions were analyzed for melatonin content using a spectrophotometer set at 277 nm. The results were reported as cumulative percent melatonin penetration. The results are shown in the table below.

| In-Vitro Penetration Through a Hydrogel | | | |
|---|---|---|---|
| Time | Cumulative % Melatonin Penetration | | |
| (hours) | Cell 1 | Cell 2 | Cell 3 |
| 1 | 21.63 | 23.07 | 21.95 |
| 3 | 37.49 | 39.73 | 41.34 |
| 5 | 52.23 | 54.47 | 56.08 |
| 7 | 62.16 | 64.08 | 66.17 |
| 24 | 102.7 | 107.5 | 109.75 |

Example 2

Melatonin (0.34 g), 2-(2-ethoxyethoxy)ethanol (2.33 g), 74:6:20 isooctyl acrylate:acrylamide:vinyl acetate adhesive copolymer and 90:10 ethyl acetate:methanol (14.37 g) were combined in a glass jar. The glass jar was placed on a platform shaker and shaken until a homogeneous formulation was obtained. The formulation was allowed to stand until all of the air bubbles had dissipated. The formulation was knife coated at a thickness of 500 μM (20 mils) onto a silicone coated release liner. The resulting coated release liner was oven dried for 2 minutes at 52° C., for 2 minutes at 85° C. and for 2 minutes at 108° C. The resulting adhesive coating contained 5 percent by weight of melatonin, 35 percent by weight of 2-(2-ethoxyethoxy)ethanol and 60 percent by weight of 74:6:20 isooctyl acrylate:acrylamide:vinyl acetate adhesive copolymer. The material was allowed to cool and was then laminated onto the corona treated surface of a low density polyethylene backing.

Example 3

Using the general method of Example 2, sheet material coated with an adhesive coating containing 5 percent by weight of melatonin, 34 percent by weight of 2-(2-ethoxyethoxy)ethanol, 1 percent by weight of N,N-dimethyldodecylamine-N-oxide and 60 percent by weight of 74:6:20 isooctyl acrylate:acrylamide:vinyl acetate adhesive copolymer was prepared.

Example 4

Using the general method of Example 2 except that 70:30 heptane:isopropanol was used as the solvent, sheet material coated with an adhesive coating containing 3 percent by weight of melatonin, 35 percent by weight of 2-(2-ethoxyethoxy)ethanol, 2 percent by weight of N,N-dimethyldodecylamine-N-oxide and 60 percent by weight of 74:6:20 isooctyl acrylate:acrylamide:vinyl acetate adhesive copolymer was prepared.

Example 5

Using the general method of Example 4, sheet material coated with an adhesive coating containing 1 percent by weight of melatonin, 36 percent by weight of 2-(2-ethoxyethoxy)ethanol, 3 percent by weight of N,N-dimethyldodecylamine-N-oxide and 60 percent by weight of 74:6:20 isooctyl acrylate:acrylamide:vinyl acetate adhesive copolymer was prepared.

In-vitro Penetration Through Hairless Mouse Skin

Although animal skins are known to give significant quantitative differences in drug penetrability as compared to human skin, a rank order correlation is generally observed with various drugs (M. J. Bartek and J. A. LaBudde in "Animal Models in Dermatology" H Maibach, Ed , Churchill Livingstone, New York, 1975, pp. 103–119). Hairless mouse skin has been recommended as a readily available animal skin for use in diffusion cells with steroids and other small molecules (R. B. Stoughton, *Arch. Derm.*, 99, 753 (1969), J. L. Cohen and R. B. Stoughton, *J. Invest. Derm.*, 62, 507 (1974), R. B. Stoughton in "Animal Models in Dermatology", pp. 121–131. In the specific test procedure used herein, hairless mouse skin removed from female hairless mice that were 4–6 weeks old was used. The skin was maintained on ice until use, and it was preferably used within 8 hours of sacrifice. The mouse skin was mounted on a diffusion cell of the type shown in the Drawing. As shown in the Drawing, mouse skin 20 was mounted epidermal side up between upper portion 21 and lower portion 22 of the cell, which are held together by means of ball joint clamp 23.

The portion of the cell below the mounted skin was completely filled with receptor fluid (phosphate buffered saline as prepared in connection with penetration through a hydrogel described above) such that the receptor fluid contacted the skin. The receptor fluid was stirred using a magnetic stir bar 24 and a magnetic stirrer (not illustrated). The sampling port 25 was covered except when in use.

When an adhesive coated sheet material was evaluated, the skin was mounted in the diffusion cell, the release liner was removed from a 2 cm$^2$ patch and the patch was applied to the skin and pressed to cause uniform contact to the skin. Generally the patch was applied to the skin prior to the time the receptor fluid was added to the cell below the skin.

The cell was then placed in a constant temperature (32±1° C.) chamber. The receptor fluid was stirred by means of a magnetic stirrer throughout the experiment to assure a uniform sample and a reduced diffusion barrier on the dermal side of the skin. The receptor fluid was withdrawn at specified time intervals and immediately replaced with fresh fluid. The withdrawn fluid was analyzed for melatonin content using conventional high pressure liquid chromatography. The cumulative amount of melatonin penetrating the skin was calculated. Plots of the cumulative drug penetration as a function of time give a profile of the melatonin flux measured in μg/cm$^2$/hr.

The adhesive coated sheet materials prepared in Examples 2–5 were tested according to the test method described above. The results are shown in the table below where each flux value represents the average of three diffusion cells.

| In-vitro Melatonin Penetration Through Hairless Mouse Skin | |
|---|---|
| Example | Flux (μg/cm$^2$/hr) |
| 2 | 5.13 |
| 3 | 6.21 |
| 4 | 6.27 |
| 5 | 2.54 |

What is claimed is:

1. An adhesive coated sheet material comprising a backing bearing on one surface thereof a pressure sensitive adhesive coating comprising a homogeneous mixture of
   (i) a copolymer comprising
      (1) about 60 to 80 percent by weight of a monomeric acrylic or methacrylic acid ester of an alkyl alcohol containing 4 to 10 carbon atoms, based on the weight of all monomers in the copolymer;
      (2) about 4 to 9 percent by weight of a monomer selected from the group consisting of acrylic acid, methacrylic acid, an alkyl acrylate or methacrylate containing 1 to 3 carbon atoms in the alkyl group, acrylamide, methacrylamide, a lower alkyl substituted acrylamide, diacetone acrylamide, and N-vinyl-2-pyrrolidone, based on the weight of all monomers in the copolymer; and
      (3) about 15 to 35 percent by weight of vinyl acetate, based on the weight of all monomers in the copolymer;
   (ii) a therapeutically effective amount of melatonin; and
   (iii) a skin-penetration enhancing amount of 2-(2-ethoxyethoxy)ethanol.

2. An adhesive coated sheet material according to claim 1, wherein the 2-(2-ethoxyethoxy)ethanol is present in an amount of about 30 to 40 percent by weight based on the total weight of the adhesive coating.

3. An adhesive coated sheet material according to claim 1, wherein the melatonin is present in an amount of about 1 to about 10 percent by weight based on the total weight of the adhesive coating.

4. An adhesive coated sheet material according to claim 1, wherein the melatonin is present in an amount of about 2 to about 5 percent by weight based on the total weight of the adhesive coating.

5. An adhesive coated sheet material according to claim 1, wherein the copolymer comprises the acrylic or methacrylic acid ester in an amount of about 70 to 80 percent by weight based on the total weight of all monomers in the copolymer.

6. An adhesive coated sheet material according to claim 1, wherein the copolymer comprises isooctyl acrylate.

7. An adhesive coated sheet material according to claim 1, wherein the copolymer comprises acrylamide.

8. An adhesive coated sheet material according to claim 1, wherein the copolymer comprises vinyl acetate in an amount of about 15 to 25 percent by weight based on the total weight of all monomers in the copolymer.

9. An adhesive coated sheet material according to claim 1, wherein the adhesive coating further comprises a skin-penetration enhancing amount of N,N-dimethyldodecylamine-N-oxide.

10. An adhesive coated sheet material according to claim 9, wherein the N,N-dimethyldodecylamine-N-oxide is present in an amount of about 1 to 3 percent based on the total weight of the adhesive coating.

11. An adhesive coated sheet material according to claim 9, wherein the melatonin is present in an amount of about 1 to about 10 percent by weight based on the total weight of the adhesive coating.

12. An adhesive coated sheet material according to claim 9, wherein the melatonin is present in an amount of about 2 to about 5 percent by weight based on the total weight of the adhesive coating.

13. An adhesive coated sheet material according to claim 9, wherein the copolymer comprises the acrylic or methacrylic acid ester in an amount of about 70 to 80 percent by weight based on the total weight of all monomers in the copolymer.

14. An adhesive coated sheet material according to claim 9, wherein the copolymer comprises isooctyl acrylate.

15. An adhesive coated sheet material according to claim 9, wherein the copolymer comprises acrylamide.

16. An adhesive coated sheet material according to claim 9, wherein the copolymer comprises vinyl acetate in an amount of about 15 to 25 percent by weight based on the total weight of all monomers in the copolymer.

17. An adhesive coated sheet material comprising a backing bearing on one surface thereof a pressure sensitive adhesive coating comprising a homogeneous mixture of
(i) a copolymer comprising about 74 percent by weight of isooctyl acrylate based on the total weight of all monomers in the copolymer, about 6 percent by weight of acrylamide based on the total weight of all monomers in the copolymer, and about 20 percent by weight of vinyl acetate based on the total weight of all monomers in the copolymer;
(ii) melatonin in an amount by weight of about 3 percent based on the total weight of the adhesive coating;
(iii) 2-(2-ethoxyethoxy)ethanol in an amount by weight of about 35 percent based on the total weight of the adhesive coating; and
(iv) N,N-dimethyldodecylamine-N-oxide in an amount by weight of about 2 percent based on the total weight of the adhesive coating.

18. A method of treating in an animal a condition capable of treatment by melatonin comprising the steps of:
(i) providing an adhesive coated sheet material according to claim 1;
(ii) applying the adhesive coated sheet material to the skin of the animal; and
(iii) allowing the adhesive coated sheet material to remain on the skin in order to establish or maintain a therapeutically effective blood level of melatonin.

19. A method of preventing and/or relieving migraine headache in a patient, comprising the steps of:
(i) providing an adhesive coated sheet material according to claim 1;
(ii) applying the adhesive coated sheet material to the skin of the patient; and
(iii) allowing the adhesive coated sheet material to remain on the skin in order to establish or maintain a blood level of melatonin effective to prevent and/or relieve migraine headache.

* * * * *